US011110142B2

(12) United States Patent
Shimoide (10) Patent No.: US 11,110,142 B2
(45) Date of Patent: *Sep. 7, 2021

(54) KAMPO MEDICINE FOR IMPROVING COGNITIVE FUNCTION IN ALZHEIMER-TYPE DEMENTIA OR MILD COGNITIVE IMPAIRMENT AND TREATING AT LEAST ONE DISEASE FROM THE GROUP CONSISTING OF OVERACTIVE BLADDER, CONSTIPATION, AND CHRONIC KIDNEY DISEASES COMPLICATED BY THEM WITH ONE DRUG

(71) Applicant: Yoshiteru Shimoide, Kogoshima (JP)

(72) Inventor: Yoshiteru Shimoide, Kogoshima (JP)

( * ) Notice: Subject to any disclaimer, the term of this patent is extended or adjusted under 35 U.S.C. 154(b) by 63 days.

This patent is subject to a terminal disclaimer.

(21) Appl. No.: 16/777,534

(22) Filed: Jan. 30, 2020

(65) Prior Publication Data

US 2020/0164017 A1 May 28, 2020

Related U.S. Application Data

(63) Continuation of application No. 16/210,343, filed on Dec. 5, 2018, now Pat. No. 10,660,929.

(30) Foreign Application Priority Data

Mar. 30, 2018 (JP) .............................. JP2018-069196

(51) Int. Cl.
| | | |
|---|---|---|
| *A61K 36/00* | (2006.01) | |
| *A61K 36/718* | (2006.01) | |
| *A61P 25/28* | (2006.01) | |
| *A61P 1/10* | (2006.01) | |
| *A61P 13/10* | (2006.01) | |
| *A61P 13/12* | (2006.01) | |
| *A61K 36/076* | (2006.01) | |
| *A61K 36/284* | (2006.01) | |
| *A61K 36/484* | (2006.01) | |
| *A61K 36/54* | (2006.01) | |
| *A61K 36/488* | (2006.01) | |
| *A61K 36/744* | (2006.01) | |
| *A61K 36/539* | (2006.01) | |
| *A61K 36/756* | (2006.01) | |

(52) U.S. Cl.
CPC .......... *A61K 36/718* (2013.01); *A61K 36/076* (2013.01); *A61K 36/284* (2013.01); *A61K 36/484* (2013.01); *A61K 36/488* (2013.01); *A61K 36/539* (2013.01); *A61K 36/54* (2013.01); *A61K 36/744* (2013.01); *A61K 36/756* (2013.01); *A61P 1/10* (2018.01); *A61P 13/10* (2018.01); *A61P 13/12* (2018.01); *A61P 25/28* (2018.01)

(58) Field of Classification Search
None
See application file for complete search history.

(56) References Cited

U.S. PATENT DOCUMENTS

| 2014/0234366 A1 | 8/2014 | Shimoide |
| 2014/0370134 A1 | 12/2014 | Li et al. |

FOREIGN PATENT DOCUMENTS

| CN | 101274059 A | * 10/2008 |
| CN | 101 450 201 A | 6/2009 |
| CN | 107 715 044 A | 2/2018 |
| JP | H06-211680 A | 8/1994 |
| JP | 2015-508052 A | 3/2015 |
| JP | 6154566 B1 | 6/2017 |

OTHER PUBLICATIONS

Boyd et al., "Clinical Practice Guidelines and Quality of Care for Older Patients with Multiple Comorbid Diseases: Implications for Pay for Performance," *JAMA*, vol. 294, No. 6, dated Aug. 10, 2005, 9 pages.
Salive, "Multimorbidity in Older Adults," *American Journal of Epidemiology*, vol. 35, No. 1, Jan. 1, 2013, pp. 75-83, date published Jan. 31, 2013.
Anthierens et al., "Qualitative insights into general practitioners views on polypharmacy," *BMC Family Practice*, vol. 11, No. 65, 2010, 6 pages.
Fushiki et al., "Polypharmacy and Adverse Drug Events Leading to Acute Care Hospitalization in Japanese Elderly," *General Medicine*, vol. 15, No. 2, 2014, pp. 110-116, accepted in revised form Oct. 26, 2014.
Green et al., "Is the Number Of Prescribing Physicians an Independent Risk Factor for Adverse Drug Events in an Elderly Outpatient Population?" *The American Journal of Geriatric Pharmacotherapy*, vol. 5, No. 1, Mar. 2007, date accepted for publication Jan. 25, 2007, pp. 31-39.
Smith et al., "Managing patients with multimorbidity: systematic review of interventions in primary care and community settings," *BMJ*, 345, e5205, 2012, published Sep. 3, 2012, 10 pages.
Boyd et al., "Multimorbidity Pattern Analysis and Clinical Opportunities: Dementia," *CHCS Center for Health Care Strategies, Inc.*, Dec. 2010, 21 pages.
Sasamori et al., "Reports of Aggregate Results of Health Screening in Japan, 2014," *Health Screening*, 30, 2015, including partial English translation, 15 pages.

(Continued)

*Primary Examiner* — Qiuwen Mi
(74) *Attorney, Agent, or Firm* — Crowell & Moring, LLP (57) ABSTRACT

Provided is a kampo medicine for treating multimorbidity of Alzheimer-type dementia or mild cognitive impairment and at least one disease from the group consisting of overactive bladder, constipation, and chronic kidney disease with one drug. A kampo medicine for treating multimorbidity with one drug, comprising a drug combination of orengedokuto and ryokeijutsukanto as an active ingredient, wherein the kampo medicine improves a cognitive function in Alzheimer-type dementia or mild cognitive impairment and relieves and treats at least one disease from overactive bladder, constipation, and chronic kidney disease complicated by Alzheimer-type dementia or mild cognitive impairment at a high rate with one drug.

2 Claims, 4 Drawing Sheets

(56) References Cited

OTHER PUBLICATIONS

Ferri et al., "Global prevalence of dementia: a Delphi consensus study," *Lancet*, 366(9503):2112-7, Dec. 17, 2005.
Petersen et al., "Mild Cognitive Impairment: Clinical Characterization and Outcome," *Arch. Neurol.*, vol. 56, Mar. 1999, pp. 303-308.
Petersen et al., "Mild Cognitive Impairment as a Clinical Entity and Treatment Target," *Arch. Neurol.*, vol. 62, Jul. 2005, pp. 1160-1163.
Petersen et al., "Mild Cognitive Impairment: Aging to Alzheimer's Disease," *Oxford University Press*, 2003, 27 pages.
Petersen et al., "Vitamin E and Donepezil for the Treatment of Mild Cognitive Impairment," *The New England Journal of Medicine*, vol. 352, No. 23, Jun. 9, 2005, pp. 2379-2388.
Doody, et al., "Donepezil treatment of patients with MCI: A 48-week randomized, placebo-controlled trial," *Neurology*, vol. 72, May 5, 2009, pp. 1555-1561.
Mugie et al., "Epidemiology of constipation in children and adults: A systematic review," *Best Practice & Research Clinical Gastroenterology*, vol. 25, No. 1, 2011, pp. 3-18.
Takaue et al., "Survey of Toilet Support for Elderly People in Mie Prefecture," Fact-finding of excretion care for elderly person in MIE, vol. 9, 2007, including partial English translation, 8 pages.
Irwin et al., "Population-Based Survey of Urinary Incontinence, Overactive Bladder, and Other Lower Urinary Tract Symptoms in Five Countries: Results of the EPIC Study," *European Urology*, vol. 50, 2006, published online Oct. 2, 2006, pp. 1306-1315.
Okamura et al., "Guidelines concerning Urinary Incontinence in Elderly People," Grants-in-Aid for Scientific Research Project (Comprehensive Research Project on Longevity Science), 2000, including partial English Translation, 43 pages.
Takahashi et al., "White Matter Lesions or Alzheimer's Disease: Which Contributes More to Overactive Bladder and Incontinence in Elderly Adults with Dementia?" *J. Am. Geriatr. Soc.*, vol. 60, No. 12, pp. 2370-2371, Dec. 2012.
Imai et al., "Prevalence of Chronic Kidney Disease (CKD) in the Japanese general population predicted by the MDRD equation modified by a Japanese coefficient," *Clin. Exp. Nephrol.*, vol. 11, pp. 156-163, date accepted Jan. 30, 2007.
Seliger et al., "Moderate Renal Impairment and Risk of Dementia among Older Adults: The Cardiovascular Health Cognition Study," *J. Am. Soc. Nephrol.*, vol. 15, pp. 1904-1911, date accepted: Apr. 6, 2004.
Lannfelt et al., "Amyloid-β-directed immunotherapy for Alzheimer's disease," *J. of Internal Medicine*, vol. 275, pp. 284-295, 2014.
Okamoto et al., "Yokukan-san: a review of the evidence for use of this Kampo herbal formula in dementia and psychiatric conditions," *Neuropsychiatric Disease and Treatment*, vol. 10, pp. 1727-1742, 2014.
Supervised by Japanese Society of Neurology, Edited by "Practice Guideline for Dementia" Preparation Committee, Therapeutic Guidelines for Dementia, including partial English translation, 2017, 6 pages.
Okamoto et al., "Orengedoku-to augmentation in cases showing partial response to yokukan-san treatment: a case report and literature review of the evidence for use of these Kampo herbal formulae," *Neuropsychiatric Disease and Treatment*, vol. 9, pp. 151-155, 2013.
Nakae et al., "The Effectiveness of Hangebyakujutsutemmato for Alzheimer's Type Dementia", *Kampo Med.*, vol. 64, No. 2, pp. 104-107, 2013, including English abstract.
Iizuka et al., "Constipation and herbal medicine," *Frontiers in Pharmacology*, vol. 6, Article 73, Apr. 8, 2015, pp. 1-8.
Minagawa et al., "Status of urological Kampo medicine: A narrative review and future vision," *International Journal of Urology*, vol. 22, Jan. 18, 2015, pp. 254-263.
Zhang et al., "Astragalus (a traditional Chinese medicine) for treating chronic kidney disease," *Cochrane Database of Systematic Reviews*, 2014, vol. 10, pp. 1-21.
Kawasaki, Fumihiro, Kampo Medicine, vol. 61, Suppl. vol., 2010, dated Jun. 4, 2010, published May 2020, by *Japan Society for Oriental Medicine*, Tokyo Japan, including English translations, 6 pages.
Office Action issued in Japanese Application No. 2018-069196, dated May 15, 2018, 3 pages.
The Chinese Office Action and Search Report dated Jun. 12, 2019 in the corresponding Chinese Application No. 201811371964.1 in Chinese language.
The European Office Action dated Jul. 23, 2019 in the corresponding European Application No. 18 210 971.1.
European Search Report Action dated Jul. 9, 2019 in the corresponding European Application No. 18 210 971.1.
Mizukami, K., "Kampo therapy as an alternative to pharmacotherapy using antipsychotic medicines for behavioral and psychological symptoms of dementia (BPSD)," *Psychogeriatrics*, 8:137-141 (2008).
Peterson D., et al., "Cinnamon Extract Inhibits Tau Aggregation Associated with Alzheimer's Disease In Vitro," *Journal of Alzheimer's Disease*, 17:585-597 (2009).
Reporting letter received from Japanese associate dated Jan. 23, 2020 and the Chinese Office Action dated Nov. 13, 2019 in the corresponding Chinese Application No. 201811371964.1 (in Chinese language; machine translation in English).
Zheng, Y., et al., "The Effects of Huang-Lian-Jie-Du Decoction on the Gene Expression in the Hippocampus of Senescence-Accelerated Mouse," *Letters in Biotechnology*, 19(1):34-38 (Jan. 30, 2008) (in Chinese language; Abstract in English language; machine translation in English).
Zue, Z., "Practical Chinese Medicine—Professor Ye Jinghua's Experience in Diagnosis and Treatment of Stranguria," *Internal Medicine Magazine*, 9(4):149-150 (Dec. 25, 1995) (in Chinese language; machine translation in English).
"Sichuanchu-medic," No. 4, p. 24, (Apr. 15, 1986) (in Chinese language; machine translation in English), including: a) Deqing, L., "Guizhi Decoction for Deficiency Secrets;" b) Xuanxiao, Qui, "Linggui zhuan decoction for furuncle constipation;" and c) Bingzhang, Wu, "Raphani seed for constipation.".
Yanfeng, H., et al. "Ten Methods of Treating Kidney in Synopsis of the Golden Chamber," *China Central and Western Medical Combined Kidney Disease (CJITWN)*, 16(12):1106-1108 (Dec. 20, 2015) (in Chinese language; machine translation in English).

\* cited by examiner

KAMPO MEDICINE FOR IMPROVING COGNITIVE FUNCTION IN ALZHEIMER-TYPE DEMENTIA OR MILD COGNITIVE IMPAIRMENT AND TREATING AT LEAST ONE DISEASE FROM THE GROUP CONSISTING OF OVERACTIVE BLADDER, CONSTIPATION, AND CHRONIC KIDNEY DISEASES COMPLICATED BY THEM WITH ONE DRUG

RELATED APPLICATIONS

The present application is a continuation application of United States patent application Ser. No. 16/210,343 filed on Dec. 5, 2018, which claims priority from Japanese patent application JP 2018-69196 filed on Mar. 30, 2018, the contents of which are incorporated by reference into this application.

BACKGROUND OF THE INVENTION

1. Field of the Invention

The present invention relates to a composition for treating multimorbidity with one drug, comprising a drug combination of kampo medicines, wherein the composition improves a cognitive function in Alzheimer-type dementia or mild cognitive impairment and treats at least one disease from the group consisting of overactive bladder, constipation, and chronic kidney disease complicated by them with one drug.

2. Description of the Related Art

As in the publication by Boyd et al. in JAMA in 2005 (Boyd C. M. et al., JAMA, 294(6): 716-724, 2005), multimorbidity is defined as the coexistence of 2 or more chronic diseases simultaneously. It has been reported that 67% of 30,923,846 people who were continuously enrolled in Medicare during 2008 in U.S.A. were affected by multimorbidity and the prevalence of multiple chronic diseases increases with age to 81.5% at 85 or more years old (Marcel E. Salive et al.,: Multimorbidity in Older Adults. Epidemiology Reviews, Vol 35, Issue 1, 1 Jan. 2013, 75-83, https://doi.org/10.1093/epirev/mxs009). It has been reported that in an examination of the frequency of multimorbidity focused on only 40 chronic diseases in the U.K., 42.2% were affected by only one disease and 23.2% were affected by multimorbidity having 2 or more diseases (Anthiens S et al., BMC Fam Pract, 11:65, 2010). As a result, the existence of multiple chronic diseases naturally increases the number of administered medicines. The study of 700 elderly persons by Fushiki et al. at Jichi Medical University reported that men and women at an average age of 79.5 take an average of 6.36 drugs, and polypharmacy with 5 or more drugs was 63% (Fushiki Y et al., General Medicine, 15(2): 110-116, 2014). In addition, a cohort study by Green et al. reported that one more prescriber for a multimorbidity patient increases drug adverse events by 29% (Green J L et al., Am J Geriatr. Pharmacother, 5(1): 31-39, 2007). In other words, multimorbidity is the biggest cause of polypharmacy and polypharmacy is the biggest cause of the increase of side effects due to drugs and the increase in drug cost and medical expense, and has therefore been a global problem. Currently, guidelines for single chronic diseases exist for each of a large number of chronic diseases, but since the guidelines for single chronic diseases are not indicated for multimorbidity, the existing guidelines cannot now be used for multimorbidity. Only the guidelines having a description of recommendation for cases with multiple complications are those for diabetes and angina. It is the present conditions that no accurate guidelines for the multimorbidity exist. Studies on how to actually deal with multimorbidity is necessary (Smith S M et al., BMJ, 345: e5205, 2012) and the website of The Johns Hopkins School of Medicine emphasizes that studies for preventing multimorbidity should be promoted (Boyd C et al., Center for Health Care Strategies. Inc., 2010).

Also in Japan, it has been reported that, according to the statistics of the Japan Society of Ningen Dock (complete medical check), the super normals, who don't have abnormality in any of the basic items, were 29.8% in 1984, when the aggregation of the results started, but decreased every year to 6.6% in 2014, which was the lowest ever (Japan Society of Ningen Dock: Report on National Aggregate Results of Ningen Dock in 2014, 2014). It is considered that multimorbidity is certainly increasing and the development of the measures is urgent business.

Dementia is an intellectual disability caused by acquired causes and roughly classified into Alzheimer-type dementia, mixed dementia of Alzheimer-type dementia and cerebrovascular dementia, cerebrovascular dementia, dementia with Lewy bodies, normal pressure hydrocephalus, and frontotemporal syndromes. The main diseases of senile dementia-related diseases are Alzheimer-type dementia and cerebrovascular dementia, which account for 75% to 80% and Alzheimer-type dementia is considered to be predominantly at a higher rate. The prevalence of dementia at 30 years or older is reported to be 4 to 6% in developed regions in Europe, the Americas and the West Pacific, but increases to 20% to 33% for elderly persons at 85 years or older. Patients with dementia will continue increasing at a ratio of 4,600,000 people/year from now on and are estimated to increase to 42,300,000 in 2020 and to 81,100,000 in 2040, and it is considered that dementia will increase rapidly all over the world from now on (Ferri C P et al., Lancet, 2005; 366: 2112-2117). In other words, while Alzheimer-type dementia has been increasing, it is the biggest problem in that no therapy for dementia, including Alzheimer-type dementia, except normal pressure hydrocephalus and cerebrovascular dementia, has been established in the present, because the cause has not been determined.

Mild cognitive impairment (MCI) is a concept proposed in 1999 by Petersen et al. (Petersen R C, et al., Arch Neurol, 56: 303-308, 1999) and diagnostic criteria (Petersen R C, et al., Arch Neurol, 62: 1160-1163, 2005) newly proposed by Petersen et al. in 2003 are used for the diagnosis of mild cognitive impairment (MCI) now. In other words, mild cognitive impairment is defined to be a condition in which there are claims of cognitive decline from the subject oneself or his family, cognitive functions are not normal, but without meeting the diagnostic criteria for dementia, and there is a minimum disorder in complicated daily life movements, but basic everyday life can be spent normally. In other words, no behavior and psychological symptoms of dementia (BPSD) is observed in mild cognitive impairment (MCI). It has been reported that as a result of a follow-up study by Petersen et al. at Mayo Clinic of subjects with MCI by their criteria for 15 years or more, the subjects progressed to dementia or probable AD at an average ratio of 12% per year and about 80% developed dementia in 6 years (Petersen R C, et al., Mild cognitive impairment, New York: Oxford UP; 2003, P. 15-39). From this result, it is considered that improving mild cognitive impairment (MCI) would naturally reduce the patients who develop Alzheimer-type dementia. However, the results of clinical trials with donepezil hydrochloride for MCI were reported in 2005, and it was reported that progress of dementia can significantly be suppressed by intake of donepezil hydrochloride for one year, but there is no preventive effect on the disease progression afterward (Petersen R C et al., N Engl J Med, 2005: 352: 2379-88), indicating that administration of donepezil hydrochloride eventually results in the same course of cognitive decline as that without treatment after one year. In other words, like there is no effective drug that improves cognitive functions in Alzheimer-type dementia developed, no effective drug that ameliorates cognitive decline has been successfully developed also for mild cognitive impairment (MCI) (Doody R S et al., Neurology, 72: 1555-1561, 2009).

Multimorbidity is easy to occur in Alzheimer-type dementia or mild cognitive impairment and complications with constipation and/or overactive bladder are developed at a high rate as an autonomic nervous system disorder. In other words, the frequency of normal chronic constipation is reported to be 0.7 to 79% (median 16%) according to systematic review (Mugie S M et al., Best Pract Res Clin Gastroenterol, 25(1): 3-18, 2011). Since most of patients with Alzheimer-type dementia or mild cognitive impairment are old in age, constipation is a frequently observed complication. It has been reported that among 7,758 elderly persons in nursing facilities or at home, 73.7% have cognitive impairment and 1,967 persons (25.4%) have constipation (Takaue Sachiko et al.: Fact-finding of excretion care for elderly person in Mie Prefecture. Mie nursing journal, 9:111-116, 2007).

As to overactive bladder, Irwin et al. have reported that 11.8% of general population at 18 years or older has overactive bladder and the frequency increases with age (Debra E. Irwin et al., European Urology, 50: 1306-1315, 2006) and it has been reported that incontinence is very common in elderly persons and it is observed in 5 to 10% of at-home elderly persons and about 50% of elderly persons in institution (Kikuo Okamura, et al., Guidelines on Urinary Incontinence in the Elderly (http://www.ncgg.go.jp/hospital/iryokankei/documents/guidelines.pdf), P. 6-15). Furthermore, it has been reported that 44% of patients with Alzheimer-type dementia have nocturia, which is one of the diagnostic criteria for overactive bladder (Takahashi O et al., J Am Geriatr Soc, 60: 2370-2371, 2012).

Furthermore, the number of patients with chronic kidney disease (CKD) in U.S.A. is about 13% of the adult population according to National Health and Nutrition Examination Survey (NHANES). In Japan, the number of patients with chronic kidney disease (CKD) is reported to be 13% of the adult population and 13 million persons (Imai, E., et al., Clin. Exp. Nephrol., 11(2), 156-163, 2007). Cardiovascular Health Cognition Study has indicated that moderate renal dysfunction increases development of dementia by 37% (Seliger S L, et al., J Am Soc Nephrol, 15: 1904-1911, 2004). Furthermore, most of Alzheimer-type dementia patients are easy to have decreased renal functions due to the age since they are old and easy to have complications with chronic kidney disease (CKD).

In other words, Alzheimer-type dementia and mild cognitive impairment are complicated by constipation and overactive bladder at high rates due to autonomic nervous system disorders, and complications with chronic kidney disease are found frequently and multimorbidity is observed frequently. However, no effective guidelines for any combination of Alzheimer-type dementia or mild cognitive impairment and complication diseases thereof and no therapeutic agents specific for this multimorbidity exist.

Only therapeutic drugs for Alzheimer-type dementia are 3 acetylcholinesterase inhibitors (donepezil hydrochloride, galanthamine, rivastigmine) and 1 low affinity N-methyl-D-asparagine receptor antagonist (memantine). These are medicines for ameliorating symptoms and the effect of any drug on cognitive function is transient. These cannot suppress progression of Alzheimer-type dementia and no radical therapeutic effect is expected. The clinical trial with an active amyloid vaccine produced based on the hypothesis that the cause of Alzheimer-type dementia is $\beta$ amyloid, as a radical therapy, was canceled because of meningoencephalitis. In the subsequent course, it was indicated that the accumulation of amyloid $\beta$ in the brain was reduced, but the progression of dementia could not be suppressed (Lannfelt L et al., J Intern Med, 275: 284-295, 2014).

The therapeutic agents for Alzheimer-type dementia currently used in general themselves have the side effects of constipation, pollakiuria, and urinary incontinence. Therapeutic agents for overactive bladder other than mirabegron have the side effect of constipation, and solifenacin and mirabegron have the side effect of increasing creatinine. As a result, treatment of Alzheimer-type dementia and mild cognitive impairment, which are complicated by constipation, overactive bladder, and/or chronic kidney disease at a high rate is very difficult and easy to result in polypharmacy.

Even now, to patients with Alzheimer-type dementia or mild cognitive impairment complicated by constipation, overactive bladder, and/or chronic kidney disease, drugs for respective diseases are administered without any hesitation, resulting in polypharmacy. Therefore, the side effects become complicated and the frequency of side effects will be increased. It is also a problem in that the interaction of drugs has been studied only for two drugs and the interactions and side effects in polypharmacy are difficult to expect.

As to kampo medicine therapies, Jingui Yaolue written in the early third century A.D. describes an instruction to administer boijioto for dementia. However, the results of studies have indicated that administration of kampo medicines for Alzheimer-type dementia ameliorates symptoms such as behavior and psychological symptoms of dementia (BPSD), but there is no kampo medicine having a radical therapeutic effect that improves cognitive functions in the long term. Yokukansan, which is used the most often for Alzheimer-type dementia, is administered for BPSD (Hideki Okamoto et al., Neuropsychiatric Disease and Treatment, 10, 1727-1742, 2014). The 2017 Therapeutic Guidelines for Dementia by the Japanese Society of Neurology states that yokukansan is used for the suppression of BPSD in dementia with Lewy bodies (the Japanese Society of Neurology: The 2017 Therapeutic Guidelines for Dementia, 254-256, 2017). Moreover, when the BPSD suppressing effect is not obtained only with yokukansan, additional administration of orengedokuto, which is used for cerebrovascular disorder-related dementia, resulted in the suppression of BPSD, but the improvement of cognitive functions has not been described (Hideki Okamoto et al., Neuropsychiatric Disease and Treatment, 9, 151-155, 2013). In other words, this not only fails to improve cognitive functions, but also is totally far away from and unrelated to a drug for the purpose of relieving constipation, overactive bladder, and chronic kidney disease, which are other diseases that are complicated by Alzheimer-type dementia or mild cognitive impairment at high rates, with one drug and it is something totally different. There is a report that the administration of Hangebyakujutsutemmato improved cognitive functions (Yoshiharu NAKAE, et al., Kampo Med, 64, 104-107, 2013), but the observation period was 4 weeks, and it cannot relieve constipation, overactive bladder, and chronic kidney disease, which are diseases that are complicated by Alzheimer-type dementia frequently, more than considered to be only temporary like donepezil hydrochloride. In other words, despite of studies for a very long period of 1700 years to develop cognitive function-improving medicines for Alzheimer-type dementia and mild cognitive impairment, the development of a kampo medicine that improves cognitive functions has been extremely difficult and no one in the art has been able to develop a drug that ameliorates multimorbidity of constipation, overactive bladder, and chronic kidney disease, which are complicated by Alzheimer-type dementia and mild cognitive impairment frequently, with one drug.

Moreover, although various kampo medicines including Bofutsushosan have been used for constipation (Norio Iizuka et al., Frontiers in Pharmacology. 6. Article 73.2015. www.frontiersin.org) to get results, kampo medicines mainly including Goshajinkigan have been used for overactive bladder (Tomonori Miyagawa et al., Int. J Urol., 22, 254-263, 2015), and kampo therapeutics such as Boiogito have been used for chronic kidney disease (CKD) (Hong Wei Zhang, et al., Cochrane Database of Systematic Reviews, 10, 1-21, 2014), there are few medicines for overactive bladder and chronic kidney disease that have been clinically recognized and yielded long term results.

In recent years, Alzheimer-type dementia and mild cognitive impairment as well as diseases complicated by them have markedly increased. However, in multimorbidity of Alzheimer-type dementia or mild cognitive impairment, it is very difficult to relieve these diseases themselves and each individual disease of constipation, overactive bladder, and chronic kidney disease complicated by them. Moreover, since this multimorbidity is a collection of diseases in different fields that are a digestive organ disease, an urinary organ disease, and a renal disease complicated by a neurological disease, there is not even an idea of relieving these multiple diseases with one drug at the same time, and therefore there is no researcher or person skilled in the art of kampo medicines who studies drugs that can treat diseases complicated in these multimorbidity at the same time with one drug. Naturally, there is no report of research findings on these therapeutic agents for multimorbidity and consequently, there is no such drug.

SUMMARY OF THE INVENTION

The present invention provides a composition for treating multimorbidity with one drug, comprising a drug combination of orengedokuto and ryokeijutsukanto as an active ingredient, wherein the composition improves a cognitive function in Alzheimer-type dementia or mild cognitive impairment and treats at least one disease from the group consisting of overactive bladder, constipation, and chronic kidney disease complicated by them with one drug.

It has been considered to be impossible to cure complicated diseases in different fields of neurological disease, digestive organ disease, urinary organ disease, and renal disease with one drug and development of such a drug has not been conducted. The present inventors have studied diligently and developed a drug that can cure multiple diseases of any combination of Alzheimer-type dementia or mild cognitive impairment with constipation, overactive bladder, and/or chronic kidney disease at the same time with one drug, that is to say, a mixed kampo medicine of orengedokuto and ryokeijutsukanto that can treat multimorbidity of Alzheimer-type dementia or mild cognitive impairment, thereby completing the present invention.

Accordingly the present invention is as follows:

[1] A kampo medicine for treating multimorbidity with one drug, comprising a drug combination of orengedokuto (Formula antidote coptidis) and (Formula glycyrrhizae atractylodis *cinnamomi* hoelen) ryokeijutsukanto as an active ingredient, wherein the kampo medicine improves a cognitive function in Alzheimer-type dementia and relieves and treats at least one disease from overactive bladder, constipation, and chronic kidney disease complicated by Alzheimer-type dementia at a high rate with one drug.

[2] A kampo medicine for treating multimorbidity with one drug, comprising a drug combination of orengedokuto (Formula antidote coptidis) and (Formula glycyrrhizae atractylodis *cinnamomi* hoelen) ryokeijutsukanto as an active ingredient, wherein the kampo medicine improves a cognitive function in mild cognitive impairment and relieves and treats at least one disease from overactive bladder, constipation, and chronic kidney disease complicated by mild cognitive impairment at a high rate with one drug.

The composition comprising a drug combination of orengedokuto and ryokeijutsukanto as an active ingredient according to the present invention improves cognitive functions in Alzheimer-type dementia or mild cognitive impairment and relieves and treats at least one disease from the group consisting of overactive bladder, constipation, and chronic kidney disease complicated by them with one drug.

DETAILED DESCRIPTION OF THE PREFERRED EMBODIMENTS

The present invention will be described in detail below.

The composition according to the present invention is a kampo medicine which is a drug combination of orengedokuto (Formula antidote coptidis) and ryokeijutsukanto (Formula glycyrrhizae atractylodis *cinnamomi* hoelen), comprising orengedokuto and ryokeijutsukanto as an active ingredient.

Orengedokuto is a kampo medicine formulated from the crude drugs *Coptis* Rhizome (Coptidis Rhizoma), *Scutellaria* Root (*Scutellariae Radix*), *Phellodendron* Bark (*Phellodendri Cortex*), and *Gardenia* Fruit (*Gardeniae Fructus*). The mixed weights of the dried crude drugs in a daily dose for an adult are, for example, 1.5 g to 2.0 g for *Coptis* Rhizome, 3.0 g for *Scutellaria* Root, 1.5 g to 3.0 g for *Phellodendron* Bark, and 2.0 g to 3.0 g for *Gardenia* Fruit.

*Coptis* Rhizome, *Scutellaria* Root, *Phellodendron* Bark and *Gardenia* Fruit will be described below, but they may indicate things other than those set forth below. *Coptis*

Rhizome refers to a dried rhizome of *Coptis japonica* Makino in the family Ranunculaceae or another plant in the same genus, from which most of the roots have been removed. *Scutellaria* Root refers to a dried root of *Scutellaria baicalensis* Georgi in the family Labiatae, from which the periderm has been removed. *Phellodendron* Bark refers to a dried bark (phelloderm) of *Phellodendron amurense* RUPR. in the family Rutaceae or another plant in the same genus, from which the periderm has been removed. Examples of the another plant in the same genus include *Phellodendron chinense* Schneider. *Gardenia* Fruit refers to a dried fruit of *Gardenia jasminoides* ellis in the family Rubiaceae or another plant in the same genus.

Orengedokuto can be prepared by obtaining the extract preparations of the 4 crude drugs described above and mixing them according to the mixed weights described above. Alternatively, it can be prepared by putting the 4 dried crude drugs of the mixed weights described above in 600 ml of hot water, and boiling it down (concentrating) to 300 ml for one hour, the yielded 300 ml being a daily amount. The two kampo medicines, 100 ml each a time, may be mixed to 200 ml a time to be administered three times a day before every meal. The two kampo medicines, 150 ml each a time, may be mixed to 300 ml a time to be administered twice a day before morning and evening meals.

Commercial medicines are also available. The commercial medicines include OHSUGI orengedokuto Extract T Tablets (Ohsugi Pharmaceutical Co., Ltd), Kracie Orengedokuto Extract Tablets (Kracie Pharmaceutical, Ltd.), KOTARO Orengedokuto Extract Fine granules (Kotaro pharmaceutical Co., Ltd.), SAKAMOTO orengedokuto Extract granule-S(Sakamoto Kanpoh Pharmaceutical Co., Ltd.), TSUMURA Orengedokuto Extract granules for Ethical Use (TSUMURA & CO.), and JPS Orengedokuto Extract granules for Ethical Use (JPS Pharmaceutical Co., Ltd.).

Ryokeijutsukanto is a crude drug formulated from Poria *Sclerotium* (Hoelen), Atractylodes Lancea Rhizome (Atractylodis Lanceae Rhizoma) or Atractylodes Rhizome (Atractylodis Rhizoma), Cinnamon Bark (*Cinnamomi* Cortex), and *Glycyrrhiza* (Glycyrrhizae Radix). The mixed weight ratio of the dried crude drugs in a daily dose for an adult is, for example, 4 g to 6 g for Poria *Sclerotium,* 2 g to 3 g for Atractylodes Lancea Rhizome or Atractylodes Rhizome, 3 g to 4 g for Cinnamon Bark, and 1 g to 2 g for *Glycyrrhiza*. Poria *Sclerotium* and Cinnamon Bark will be described below, but they may indicate things other than those set forth below. Atractylodes Lancea Rhizome or Atractylodes Rhizome and *Glycyrrhiza* are as described above.

Poria *Sclerotium* refers to a dried *sclerotium* of Poria *cocos* Wolf in the family Polyporaceae, as it is or from which most of the shell is removed. Cinnamon Bark refers to a dried bark of *Cinnamomum cassia* Blume in the family Lauraceae or another plant in the same genus.

The extracts of the crude drugs contained in orengedokuto or ryokeijutsukanto may be, for example, extracted with water or hot water, ethanol, acetic acid from the crude drugs, dried by spray-drying or freeze-drying, and used as powder. The powders are mixed to produce orengedokuto or ryokeijutsukanto and these are mixed to produce the drug combination.

The drug combination of orengedokuto and ryokeijutsukanto may be prepared by mixing 2.5 to 10 g, preferably 5 to 10 g, more preferably 7 to 8 g, particularly preferably 7.5 g of the dried extract powder of orengedokuto and 2.5 to 10 g, preferably 5 to 10 g, more preferably 7 to 8 g, particularly preferably 7.5 g of the dried extract powder of ryokeijutsukanto for a daily adult dose. In this case, the two kampo medicines, 100 ml each a time, may be mixed to 200 ml a time to be administered three times a day before every meal. The two kampo medicines, 150 ml each a time, may be mixed to 300 ml a time to be administered twice a day before morning and evening meals. When commercial kampo medicine extracts are used, ⅓ of indicated daily doses of a commercial orengedokuto extract and a commercial ryokeijutsukanto may be mixed and administered three times a day before meals. Halves of indicated daily doses of a commercial orengedokuto extract and a commercial ryokeijutsukanto may be mixed and administered twice a day before morning and evening meals. The composition according to the present invention can be obtained by adding the mixture to an appropriate excipient, a pharmaceutic aid or the like used for usual formulation and formulate an oral formulation such as powder, a granule, a tablet, a capsule, a solution, a syrup, or the like according to a conventional method of the formulation production. Other than them, an appropriate binder, a disintegrator, a surfactant, a corrigent, and/or a flavor may be combined. Examples of the excipient include starch, dextrin, lactose, saccharose, mannite, microcrystalline cellulose, and anhydrous silicic acid.

The composition according to the present invention usually contains around 0.1 to 100% by weight of orengedokuto and ryokeijutsukanto relative to the total composition, which may vary depending on its dosage form. The dose of the composition according to the present invention to a patient may be administered once a day or divided into several divided doses and administered several times a day for several days to several tens of months or several years to ten and several years, taking the age of the patient into consideration.

The drug combination of orengedokuto and ryokeijutsukanto according to the present invention is a kampo medicine that treats at least one disease from the group consisting of Alzheimer-type dementia or mild cognitive impairment (MCI) and associating overactive bladder, constipation, and chronic kidney disease with one drug. Patients with Alzheimer-type dementia or patients with mild cognitive impairment often have complications with one, two, or three diseases selected from the group consisting of overactive bladder, constipation, and chronic kidney disease at high rates. For example, in a study with 18 patients with Alzheimer-type dementia and 22 patients with mild cognitive impairment conducted by the present inventors, 92.5% of the patients with Alzheimer-type dementia or with mild cognitive impairment had complications with any of overactive bladder, constipation, and chronic kidney disease, 82.5% had complications with overactive bladder, 72.5% had complications with constipation, and 50% had complications with chronic kidney disease. Such conditions with multiple diseases at the same time are referred to as multimorbidity. Moreover, patients having complications with all of overactive bladder, constipation, and chronic kidney disease were 32.5%, patients having complications with 2 diseases from overactive bladder, constipation, and chronic kidney disease are 47.5%, and patients having no complication with any of the diseases were 7.5%. The drug combination of orengedokuto and ryokeijutsukanto according to the present invention may improve the cognitive function of patients with Alzheimer-type dementia or mild cognitive impairment and relieve and treat one, two or three diseases from the group consisting of overactive bladder, constipation, and chronic kidney disease complicated by Alzheimer-type dementia or mild cognitive impairment. Accordingly, the drug combination of orengedokuto and ryokeijutsukanto according to the present invention is a kampo medicine for treating multimorbidity of Alzheimer-type dementia or mild cognitive impairment and at least one disease from the group consisting of overactive bladder, constipation, and chronic kidney disease with one drug.

Alzheimer-type dementia refers to dementia manifested in patients with Alzheimer's disease, which is a neurodegenerative disease that causes brain atrophy.

Mild cognitive impairment corresponds to the stage before dementia, considered to be an intermediate stage between a healthy subject and dementia, and refers to a condition in which the cognitive function is lowered than that expected in the normal aging process but not as low as to be called dementia. Definitions of mild cognitive impairment include the following three: 1. the person oneself or his family claims cognitive decline (memory, judgment, reasoning, execution); 2. the cognitive function is not normal, but without meeting diagnostic criteria for dementia; and 3. there is a minimum disorder in complicated daily life movements, but everyday life can be spent normally.

Alzheimer-type dementia and mild cognitive impairment can be diagnosed by Hasegawa Dementia Scale (HDS-R) and Mini Mental State Examination (MMSE). Hasegawa Dementia Scale (HDS-R) is a test for investigating a tendency of dementia from the result of test of total 30 points with total 9 items. MMSE is a test of total 30 points with 13 questions of 9 items that covers orientation, memory, calculation, language ability, graphic ability, and the like.

If the result of an HDS-R test is 20 points or more, then the cognitive function is normal and it can be determined that Alzheimer-type dementia or mild cognitive impairment has been ameliorated.

Overactive bladder refers to dysuria with a feeling of urinary urgency by bladder's involuntary contractions. Overactive bladder is diagnosed, for example, when there is a feeling of urinary urgency and the frequency of urination at night is 3 times or more. It can be determined that overactive bladder is relieved and successfully treated when the frequency of urination at night is once or less.

Constipation refers to infrequent bowel movements caused by various causes such as lifestyles, diseases, side effects of drugs, and the like. It can be determined whether a subject has constipation or not based on Rome III diagnostic criteria (Longstreth G F, et al., Gastroenterology 130: 1480-1491, 2006). It can be determined whether constipation is relieved and successfully treated based on the criteria.

Chronic kidney disease (CKD) refers to a condition in which a kidney disorder continues chronically. Chronic kidney disease is diagnosed when there is persistence of any or both of a renal disorder (occurrence of proteinuria or bloody urine, observation of injury by diagnostic imaging, or the like) and a lowered renal function (an eGFR (estimated glemerular filtration rate) of less than 60 ml/min./1.73 m$^2$) for 3 months or more. For example, when the eGFR (estimated glemerular filtration rate) is 60 ml/min./1.73 m$^2$ or more, it can be determined that chronic kidney disease is relieved and successfully treated.

As to the dose of the drug combination of orengedokuto and ryokeijutsukanto according to the present invention, for example, when commercial medical kampo medicine extract formulations are used at a daily dose of 7.5 g for an adult, a mixed drug combination of 2.5 g each of the kampo medicines may be orally administered three times a day before meal. The medicines are administered until symptoms of the patient are relieved, which varies depending on the reaction of the patient.

Furthermore, the composition according to the present invention may be admixed into food or a beverage and used as a food or drink composition or a feeding-stuff composition. In such a use, orengedokuto and ryokeijutsukanto may be mixed into a single intake amount of the food or drink or feeding-stuff, for example, at a ratio of 100 mg/kg, when the daily dose of commercial medical kampo medicine extracts for a person is 7.5 g. The composition according to the present invention may be used as a food or drink composition or a feeding-stuff composition in a form of powder, granules, liquid, paste, or the like. Beverages and foods include foods with function claims, health beverages and foods, beverages and foods for specified health uses, functional nutritional beverages and foods, and beverage or food supplements. As used herein, foods for specified health uses refer to foods that are taken for a specific health purpose in diets and have an indication that the health purpose may be achieved by the intake. Moreover, foods with function claims refer to foods displaying functionality on their product packages based on a chemical basis on the responsibility of the organization of the products. The composition according to the present invention may have a display indicating, for example, "maintaining cognitive functions", "maintaining a part of cognitive functions", "ameliorating constipation", "ameliorating dysuria", "ameliorating overactive bladder", "improving renal functions", or "maintaining cognitive functions and ameliorating or improving any one, two, or three of constipation, overactive bladder or dysuria, and renal functions".

EXAMPLES

The present invention will be specifically described by the following Examples, but the present invention is not limited by these Examples.

In Examples, commercial kampo medicine extracts (TSUMURA & CO.) were used and a mixed kampo medicine of orengedokuto and ryokeijutsukanto containing 7.5 g of orengedokuto dried extract powder and 7.5 g of ryokeijutsukanto dried extract powder was administered as a daily dose.

1. Subject

The subjects were 49 patients with cognitive impairment (22 patients with Alzheimer-type dementia, 27 patients with mild cognitive impairment) (male:female=5:44) followed and assessed from Jun. 18, 2002 to Jul. 27, 2017, 82.0±1.1 years old in average age. Among 49 patients, 9 patients were in the control group (4 patients with Alzheimer-type dementia, 5 patients with mild cognitive impairment) and 40 patients were in the treatment group of the mixed kampo medicine of orengedokuto and ryokeijutsukanto (18 patients with Alzheimer-type dementia, 22 patients with mild cognitive impairment). All the 49 subjects had multiple complications, but among 40 patients in the treatment group of the mixed kampo medicine of orengedokuto and ryokeijutsukanto, 92.5% (37/40) had complications with any of constipation, overactive bladder, and chronic kidney disease (17 patients of 18 patients with Alzheimer-type dementia, 20 patients of 22 patients with mild cognitive impairment), 72.5% (29/40) had complications with constipation (12 patients of 18 patients with Alzheimer-type dementia, 17 patients of 22 patients with mild cognitive impairment), 82.5% (33/40) had complications with overactive bladder (15 patients of 18 patients with Alzheimer-type dementia, 18 patients of 22 patients with mild cognitive impairment), and 50% (20/40) had chronic kidney disease (9 patients of 18 patients with Alzheimer-type dementia, 11 patients of 22 patients with mild cognitive impairment). Moreover, 13 patients had complications with 3 diseases, 19 patients had complications with 2 diseases, 5 patients had complications with 1 disease, 3 patients had no complication with any of the 3 diseases. Among 9 patients in the control group, 88.9% (8/9) had complications with any of constipation, overactive bladder, and chronic kidney disease, 55.6% (5/9) had complications with constipation, 33.3% (3/9) had complications with overactive bladder, 55.6% (5/9) had complications with chronic kidney disease, 1 patient had complications with the 3 diseases of constipation, overactive bladder, and chronic kidney disease, 3 patients had complications with 2 diseases, 4 patients had complications with 1 disease, and 1 patient had no complication with any of the 3 diseases.

2. Method

Alzheimer-type dementia of the subjects was clinically diagnosed by diagnostic criteria in the ICD-10 and diagnostic imaging such as head MRI, and mild cognitive impairment was clinically diagnosed by the diagnostic criteria by Petersen et al. in 2003 (Petersen R C, et al., Arch Neurol 62: 1160-1163, 2005) and diagnostic imaging such as head MRI. Since the correlation between Hasegawa Dementia Scale-Revised (HDS-R) and Mini-Mental-State Examination (MMSE) was 0.94 and very high (Shinji Kato, et al., Development of the revised version of Hasegawa's Dementia Scale (HDS-R), Japanese journal of geriatric psychiatry, vol. 2, issue 11, 1339-1347. 1991), and the discrimination of dementia was highly reproducible regardless of the age and the duration of education in year with a sensitivity and a specificity of 0.90 and 0.82 respectively, when the cut-off value for HDS-R was set to 20/21 points, the disease course and the therapeutic effect were scored and expressed with HDS-R taking objectivity into consideration highly.

Constipation was classified and diagnosed based on ROME III (Longstreth G F, et al., Gastroenterology 130: 1480-1491, 2006).

Overactive bladder was diagnosed by using Clinical guidelines for overactive bladder by the Japanese Continence Society and the course was observed by Overactive Bladder Symptom Score (OABSS). Since many patients use diapers and there were obstacles for diagnosis, overactive bladder was diagnosed when there is a feeling of urinary urgency and the number of nighttime urination was 3 times or more. When the administration of a mixed kampo medicine of orengedokuto and ryokeijutsukanto resulted in one time or less of nighttime urination, it was determined as effective. As to the determination of therapeutic effect on constipation, it was determined effective when the bowel movement occurred once in 2 days or less and the bowel movement occurred smoothly after the therapy. The chronic kidney disease was diagnosed based on Criteria for chronic kidney disease diagnosis by the Japanese Society of Nephrology revised from KDIDO CKD guideline 2012 for Japanese and the disease course was expressed by eGFR (estimated glemerular filtration rate) with the normal value of eGFR defined as 60 ml/min./1.73 $m^2$ or more. The established diagnostic criteria were adapted for the cases for which the course had been observed since before the establishment of diagnostic criteria and expressed.

The drug used was a mixed kampo medicine of orengedokuto and ryokeijutsukanto and the efficacy was determined by comparing before and after administration and with the control group. The observation period of the 49 subjects was 810.0±126.0 days (56 days to 4,883 days) and the observation period of the administration group of the mixed kampo medicine of orengedokuto and ryokeijutsukanto was 731.2±875.3 days. The control group was assessed for 1152±883.4 days from the start of the observation to the end of the observation (318 days to 2905 days). For the statistic processing, mean±SD or mean±SE, T-test, Chi square test were used.

3. Result

Figure 1:
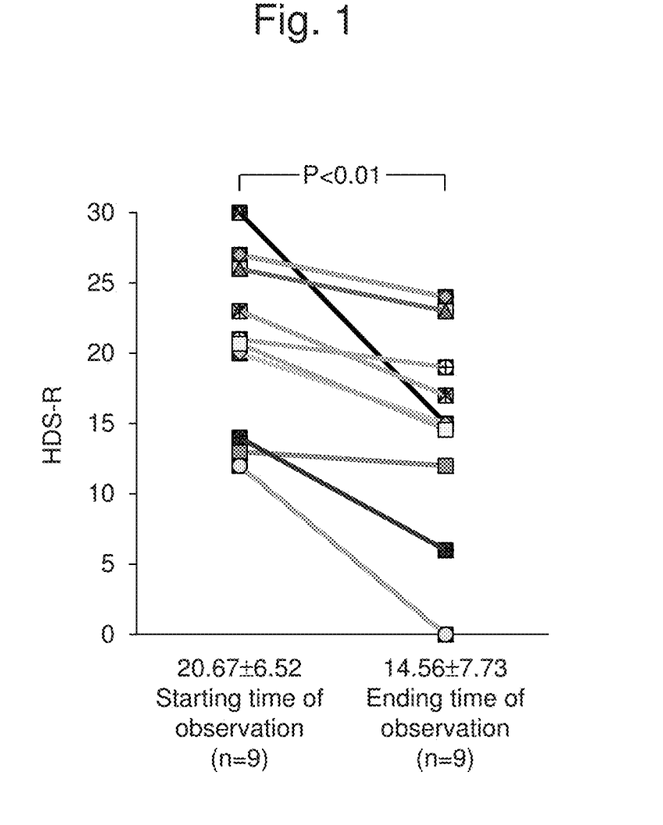
FIG. 1 illustrates comparison of HDS-R (n=9) at the starting time and the ending time of observation of the control group.
Figure 2:
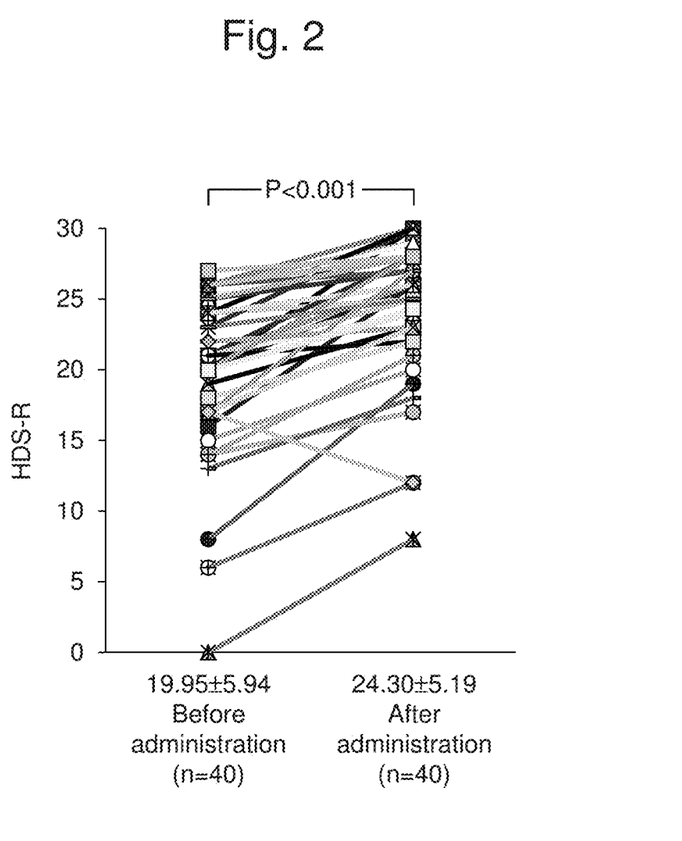
FIG. 2 illustrates comparison of HDS-R (n=40) before and after administration of a mixed kampo medicine of orengedokuto and ryokeijutsukanto.
Figure 3:
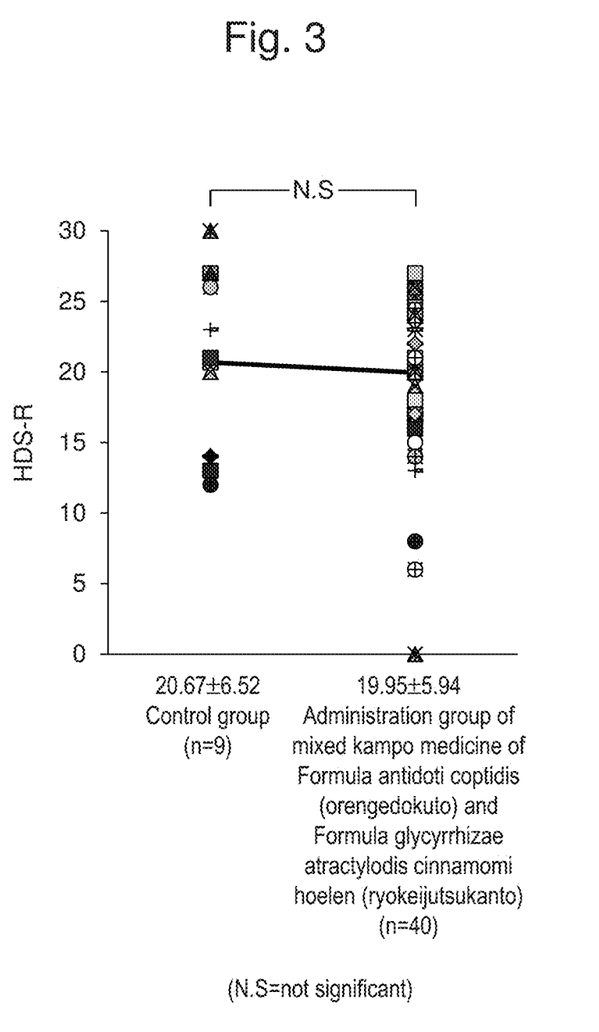
FIG. 3 illustrates comparison of HDS-R at the starting time of the observation of the control group and before the administration of the mixed kampo medicine of orengedokuto and ryokeijutsukanto.
Figure 4:
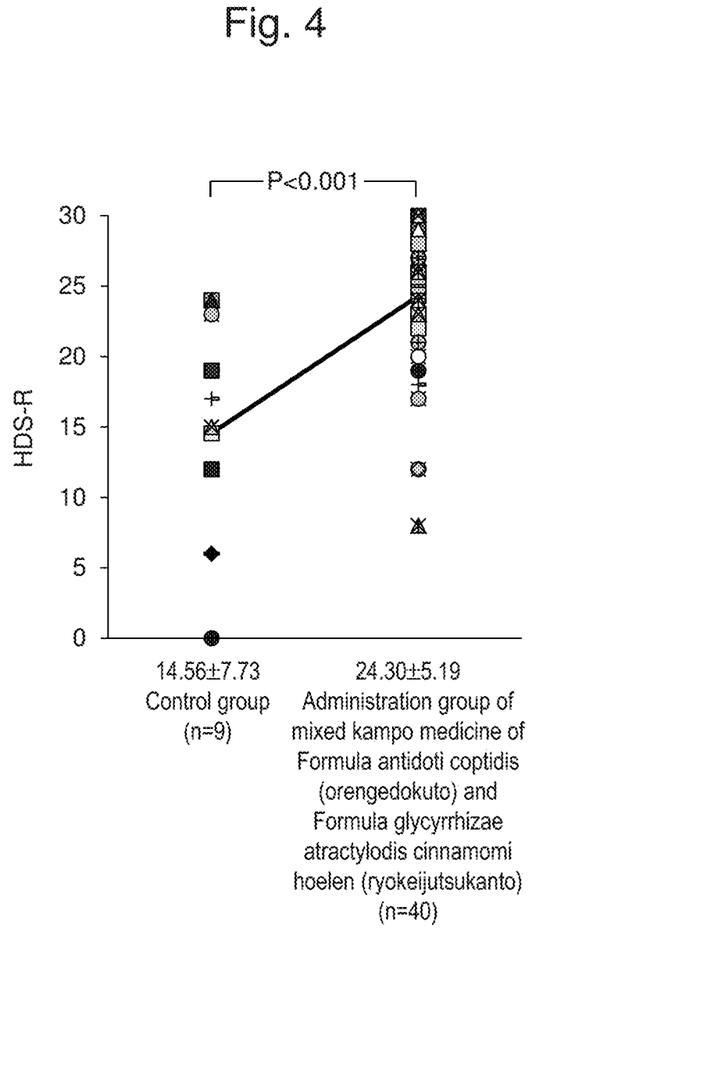
FIG. 4 illustrates comparison of HDS-R at the ending time of the observation of the control group and after the administration of the mixed kampo medicine of orengedokuto and ryokeijutsukanto.

The age and HDS-R of the control group (n=9) at the starting time of the observation were 83.56±5.25 years old and 20.67±6.52 respectively, and the age and HDS-R of the administration group of the mixed kampo medicine of orengedokuto and ryokeijutsukanto (n=40) at the starting time were 81.5±8.02 years old and 19.95±5.94 respectively. The age and HDS-R had no significant difference between the 2 groups. Moreover, the observation periods of the both groups had no significant difference. In the control group (n=9), the observation period was 1152±883.4 days and HDS-R was 20.67±6.52 at the starting time of the observation and 14.56±7.73 at the ending time of the observation, which was significantly reduced (P<0.01) (FIG. 1). In the administration group of the mixed kampo medicine of orengedokuto and ryokeijutsukanto (n=40), HDS-R in an observation period of 810.0±126.0 days was 19.95±5.94 at the starting time of the administration and 24.30±5.19 at the ending time of the observation, which indicates significant (p<0.001) restoration of cognitive functions (FIG. 2). The restoration of cognitive functions was observed in 97.5% (39/40) of the patients. There was no significant difference in HDS-R at the starting time of the observation and therapy between the control group and the administration group of the mixed kampo medicine of orengedokuto and ryokeijutsukanto (FIG. 3), but HDS-R of the administration group of the mixed kampo medicine of orengedokuto and ryokeijutsukanto was significantly higher (p<0.001) in comparison with HDS-R of the control group at the ending time of the observation (FIG. 4). In the administration group of the mixed kampo medicine, cognitive functions were also improved in the 3 patients having no complication with any of constipation, overactive bladder, and chronic kidney disease. In other words, cognitive functions were significantly restored by the administration of the mixed kampo medicine of orengedokuto and ryokeijutsukanto.

Five patients, 55.6% of the control group (n=9) had complications with constipation and none of them was relieved during the observation period. 29 patients, 72.5% of the administration group of the mixed kampo medicine of orengedokuto and ryokeijutsukanto (n=40) had constipation and 24 patients, 82.8% of the 29 patients had relief of constipation by the administration of the mixed kampo medicine of orengedokuto and ryokeijutsukanto (10 patients of 12 patients with Alzheimer-type dementia, 14 patients of 17 patients with mild cognitive impairment), indicating a significant relief from constipation by the administration of the mixed kampo medicine of orengedokuto and ryokeijutsukanto, in comparison with the control group (p<0.01).

Three patients, 33.3% of the control group (n=9) had complications with overactive bladder and none of them was relieved during the observation period. 33 patients, 82.5% of the administration group of the mixed kampo medicine of orengedokuto and ryokeijutsukanto (n=40) had complications with overactive bladder and 25 patients, 79.3% of the 33 patients (14 patients of 15 patients with Alzheimer-type dementia, 11 patients of 18 patients with mild cognitive impairment) were relieved by the administration of the mixed kampo medicine of orengedokuto and ryokeijutsukanto, indicating significant relief from overactive bladder by the administration of the mixed kampo medicine of orengedokuto and ryokeijutsukanto in comparison with the control group ($p<0.05$).

As to the chronic kidney disease, the eGFR in the control group (n=8) was 62.93±16.53 at the starting time of the observation and 52.52±14.00 at the ending time of the observation, which indicates significant ($p<0.01$) decrease, the eGFR in the administration group of the mixed kampo medicine of orengedokuto and ryokeijutsukanto (n=40) was 62.20±19.08 at the starting time of the administration and 62.00±17.59 at the ending time of the observation, with no significant difference and no decrease in eGFR. Moreover, no patients in the control group had chronic kidney disease at the starting time of the observation, but 50.0% (4/8) had chronic kidney disease at the ending time of the observation. 50% (20/40) of the patients in the administration group of the mixed kampo medicine had chronic kidney disease at the starting time of the administration of the mixed kampo medicine of orengedokuto and ryokeijutsukanto, but there was no significant decrease in eGFR after the administration of the mixed kampo medicine (46.71±2.18 vs. 48.51±2.02) (mean±SE). Furthermore, the eGFR in 13 patients, 65.0% of 20 patients, was increased by the administration of the mixed kampo medicine of orengedokuto and ryokeijutsukanto, in comparison with that at the starting time of the administration.

4. Conclusion

The mixed kampo medicine of orengedokuto and ryokeijutsukanto is a drug characterized by improving cognitive functions in Alzheimer-type dementia or mild dementia and relieving constipation, overactive bladder, and chronic kidney disease complicated by them at high rates, and being capable of treating even multimorbidity of any combination of constipation, overactive bladder, and chronic kidney disease with Alzheimer-type dementia or mild dementia.

INDUSTRIAL AVAILABILITY

By using a composition comprising a drug combination of orengedokuto and ryokeijutsukanto as an active ingredient according to the present invention, Alzheimer-type dementia or mild cognitive impairment and at least one disease from the group consisting of overactive bladder, constipation, and chronic kidney disease complicated by them can be treated with one drug.

What is claimed is:

1. A method for treating multimorbidity in a patient, comprising:
   administering to the patient one kampo combination drug consisting of a drug combination of:
   (i) orengedokuto, formulated from dried crude drugs Coptis Rhizome, Scutellaria Root, Phellodendron Bark, and Gardenia Fruit, wherein the mixed weights of the dried crude drugs in a daily dose for an adult are 1.5 g to 2.0 g for Coptis Rhizome, 3.0 g for Scutellaria Root, 1.5 g to 3.0 g for Phellodendron Bark, and 2.0 g to 3.0 g for Gardenia Fruit; and
   (ii) ryokeijutsukanto, formulated from dried crude drugs Poria Sclerotium, Atractylodes Lancea Rhizome or Atractylodes Rhizome, Cinnamon Bark, and Glycyrrhiza, wherein the mixed weights of the dried crude drugs in a daily dose for an adult are 4.0 g to 6.0 g for Poria Sclerotium, 2.0 g to 3.0 g for Atractylodes Lancea Rhizome or Atractylodes Rhizome, 3.0 g to 4.0 g for Cinnamon Bark, and 1.0 g to 2.0 g for Glycyrrhiza,
   wherein the one kampo combination drug relieves and treats at least one disease selected from the group consisting of: an overactive bladder, constipation, and chronic kidney disease.

2. A method for treating multimorbidity in a patient, comprising:
   administering to the patient one kampo combination drug consisting of a drug combination of:
   (i) orengedokuto, formulated from dried crude drugs Coptis Rhizome, Scutellaria Root, Phellodendron Bark, and Gardenia Fruit, wherein the mixed weights of the dried crude drugs in a daily dose for an adult are 1.5 g to 2.0 g for Coptis Rhizome, 3.0 g for Scutellaria Root, 1.5 g to 3.0 g for Phellodendron Bark, and 2.0 g to 3.0 g for Gardenia Fruit; and
   (ii) ryokeijutsukanto, formulated from dried crude drugs Poria Sclerotium, Atractylodes Lancea Rhizome or Atractylodes Rhizome, Cinnamon Bark, and Glycyrrhiza, wherein the mixed weights of the dried crude drugs in a daily dose for an adult are 4.0 g to 6.0 g for Poria Sclerotium, 2.0 g to 3.0 g for Atractylodes Lancea Rhizome or Atractylodes Rhizome, 3.0 g to 4.0 g for Cinnamon Bark, and 1.0 g to 2.0 g for Glycyrrhiza,
   wherein the one kampo combination drug relieves and treats constipation, and chronic kidney disease.

* * * * *